United States Patent
Sawa et al.

(10) Patent No.: US 8,074,497 B2
(45) Date of Patent: Dec. 13, 2011

(54) INDENTATION TESTING INSTRUMENT AND INDENTATION TESTING METHOD

(75) Inventors: Takeshi Sawa, Kawasaki (JP); Eiji Furuta, Kawasaki (JP)

(73) Assignee: Mitutoyo Corporation, Kawasaki (JP)

( * ) Notice: Subject to any disclaimer, the term of this patent is extended or adjusted under 35 U.S.C. 154(b) by 506 days.

(21) Appl. No.: 12/292,885

(22) Filed: Nov. 28, 2008

(65) Prior Publication Data

US 2009/0165538 A1   Jul. 2, 2009

(30) Foreign Application Priority Data

Dec. 26, 2007   (JP) ................................ 2007-334489

(51) Int. Cl.
*G01N 3/42* (2006.01)
(52) U.S. Cl. ........................................................... 73/81
(58) Field of Classification Search .............. 73/81, 104, 73/105
See application file for complete search history.

(56) References Cited

U.S. PATENT DOCUMENTS

| | | | | | |
|---|---|---|---|---|---|
| 2,363,691 | A | * | 11/1944 | Reason ............................ | 73/105 |
| 4,103,538 | A | * | 8/1978 | Stoferle et al. ..................... | 73/81 |
| 4,669,300 | A | * | 6/1987 | Hall et al. ......................... | 73/105 |
| 4,765,181 | A | * | 8/1988 | Numoto et al. ................... | 73/105 |
| 5,705,741 | A | * | 1/1998 | Eaton et al. ....................... | 73/105 |
| 5,948,972 | A | * | 9/1999 | Samsavar et al. ................ | 73/105 |
| 6,336,359 | B1 | * | 1/2002 | Kawazoe et al. .................. | 73/82 |
| 7,454,960 | B2 | * | 11/2008 | Ernst .................................. | 73/81 |
| 2009/0044609 | A1 | * | 2/2009 | Sawa et al. ......................... | 73/81 |

FOREIGN PATENT DOCUMENTS

JP   60-161508 A * 8/1985
JP   A-2004-012178   1/2004

* cited by examiner

*Primary Examiner* — Daniel Larkin
(74) *Attorney, Agent, or Firm* — Oliff & Berridge, PLC

(57) ABSTRACT

An indentation testing instrument including: a loading lever supported pivotally; an indenter provided on the loading lever; a displacement sensor movable section; a loading lever driving section; a reference lever supported pivotally having a same shaft center as the loading lever; a contactor provided on the reference lever as a positional reference of a tip portion of the indenter; a displacement sensor fixing section; a reference lever driving section; a stopper to stop the reference lever; a specimen surface reference measurement member to turn the loading lever from a state that the contactor touches the specimen surface, and to measure a first indentation depth amount; and a machine frame reference measurement member to turn the loading lever from a state that the reference lever touches the stopper and the contactor is spaced apart from the specimen surface, and to measure a second indentation depth amount.

5 Claims, 8 Drawing Sheets

INDENTATION TESTING INSTRUMENT AND INDENTATION TESTING METHOD

BACKGROUND OF THE INVENTION

1. Field of the Invention

The present invention relates to an indentation testing instrument and indentation testing method.

2. Description of Related Art

There has been known an indentation testing instrument, as a material testing machine, which forms an indentation on a specimen surface by pressing an indenter shaft provided with an indenter on a tip thereof into the specimen surface to evaluate a mechanical property such as a hardness of material (for example, see Japanese Patent Application Laid-Open Publications No. 2004-12178).

For example, the indentation testing instrument measures an indentation depth (displacement amount of the indenter) at the time when a tip of the indenter is pressed into the specimen surface with a predetermined load by a displacement gauge to evaluate the mechanical property such as the hardness of material based on a relation between the displacement amount and the load.

Since the indentation depth measured by the indentation testing instrument includes a machine frame distortion amount (machine frame compliance) due to a distortion of a machine frame of the testing instrument itself caused by the load applied to the specimen by the indentation testing instrument, it is established to perform a correction for removing the machine frame compliance, for example, by a standard such as ISO14577.

However, for example, since a method introduced in ISO14577 is a correction method based on a principle that a compliance which is an inverse of an initial unloading slope and an inverse of a square root of a contact area calculated from a curve are expressed as a linear expression passing through zero and which method presumes the machine frame compliance based on a specimen stiffness obtained from a test result, there is a problem that a correction value sometimes includes an error due to the presuming method.

Moreover, since the indentation testing instrument of Japanese Patent Application Laid-Open Publications No. 2004-12178 measures the machine frame distortion by a first displacement gauge and measures the indenter indentation depth by a second displacement gauge, a plurality of displacement gauges are needed.

SUMMARY OF THE INVENTION

An object of the present invention is to provide an indentation testing instrument and indentation testing method capable of obtaining a proper machine frame compliance to perform more precise measurement.

According to a first aspect of the present invention, an indentation testing instrument includes: a loading lever supported pivotally; an indenter provided on a lower surface of a first end of the loading lever; a displacement sensor movable section provided on an upper surface of the first end of the loading lever, the displacement sensor movable section being associated with the indenter; a loading lever driving section provided on an opposite side of the loading lever, the loading lever driving section configured to turn the loading lever; a reference lever supported pivotally so as to have a shaft center that is approximately the same as a shaft center of the loading lever; a contactor provided on a lower surface of a first end of the reference lever, the contactor being a positional reference of a tip portion of the indenter; a displacement sensor fixing section provided on an upper surface of the first end of the reference lever, the displacement sensor fixing section configured to detect a displacement amount of the displacement sensor movable section; a reference lever driving section provided on an opposite end of the reference lever, the reference lever driving section configured to turn the reference lever; a stopper to stop the reference lever so that the contactor is in a predetermined position with respect to a specimen surface; a specimen surface reference measurement member configured to turn the loading lever from a state that the contactor touches the specimen surface, and configured to measure a first indentation depth amount at a time when the indenter touching the specimen surface is pressed against the specimen by detecting the displacement amount of the displacement sensor movable section with the displacement sensor fixing section; and a machine frame reference measurement member configured to turn the loading lever from a state that the reference lever touches the stopper and the contactor is spaced apart from the specimen surface, and configured to measure a second indentation depth amount at a time when the indenter touching the specimen surface is pressed against the specimen.

According to a second aspect of the preferred embodiment of the present invention, an indentation testing method in the indentation testing instrument includes: obtaining a machine frame compliance of the indentation testing instrument by subtracting the first indentation depth amount measure by the specimen surface reference measurement member from the second indentation depth amount measured by the machine frame reference measurement member; obtaining a correlation function between the load and the machine frame compliance by obtaining the machine frame compliance with respect to each of the load for pressing the indenter against the specimen in the machine frame compliance obtaining step; and obtaining a corrected indentation depth amount by subtracting the machine frame compliance with respect to the loading as measuring the second indentation depth amount from the second indentation depth amount with respect to an arbitrary load measured by the machine frame reference measurement member based on the correlation function obtained in the correlation function obtaining step.

BRIEF DESCRIPTION OF THE DRAWINGS

The present invention will become more fully understood from the detailed description given hereinbelow and the appended drawings which given by way of illustration only, and thus are not intended as a definition of the limits of the present invention, and wherein.

DETAILED DESCRIPTION OF THE INVENTION

In the following, an indentation testing instrument and indentation testing method according to the present invention will be described in detail with reference to drawings.

Incidentally, an indentation testing instrument 100 of this embodiment is an instrumented indentation testing instrument capable of monitoring a test force (load) applied to an indenter 4 and an indentation depth of the indenter 4 sequentially.

Figure 1:
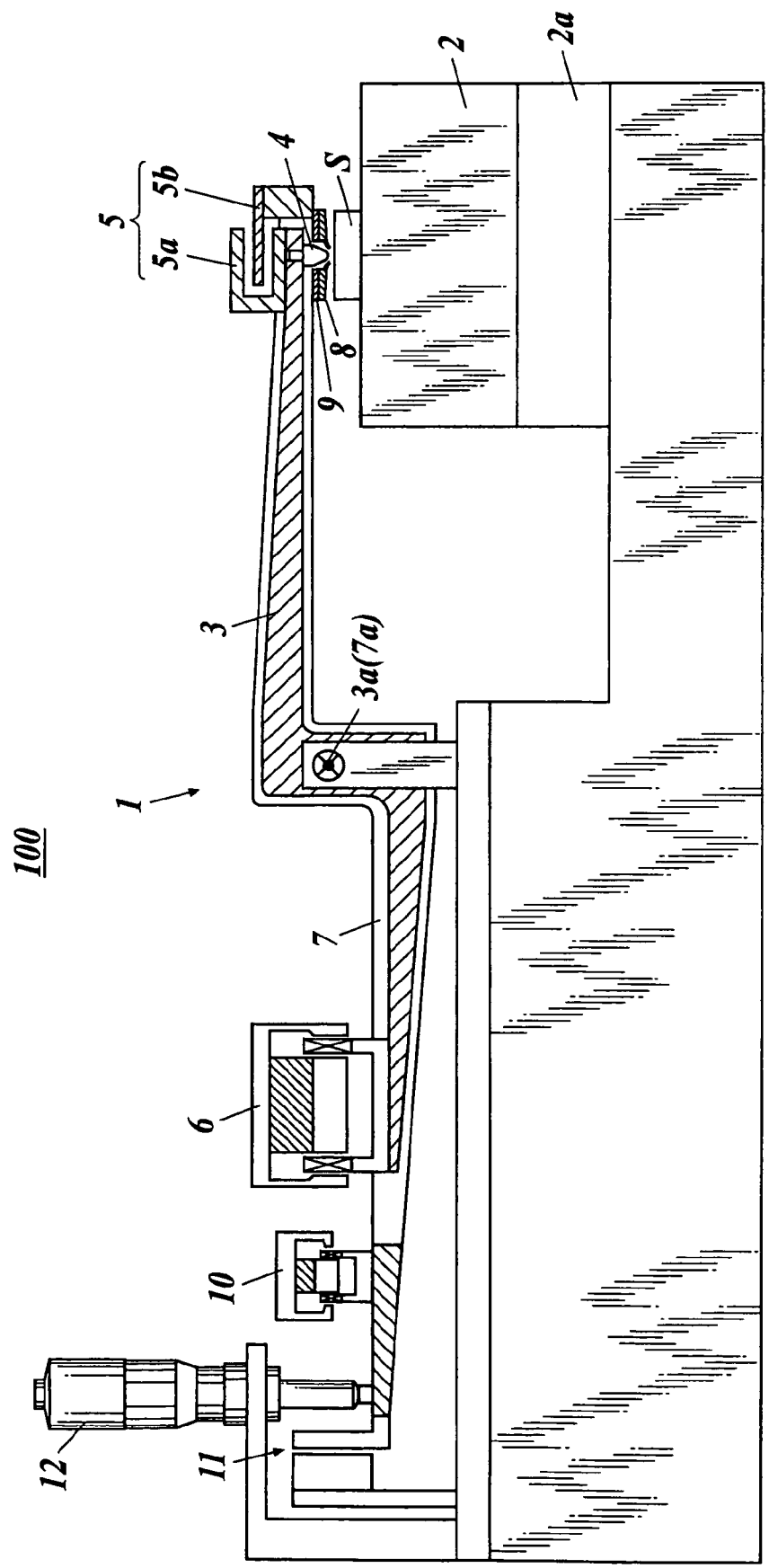
FIG. 1 is a side view showing a cross section of a part of an indentation testing instrument according to the present invention.
Figure 2:
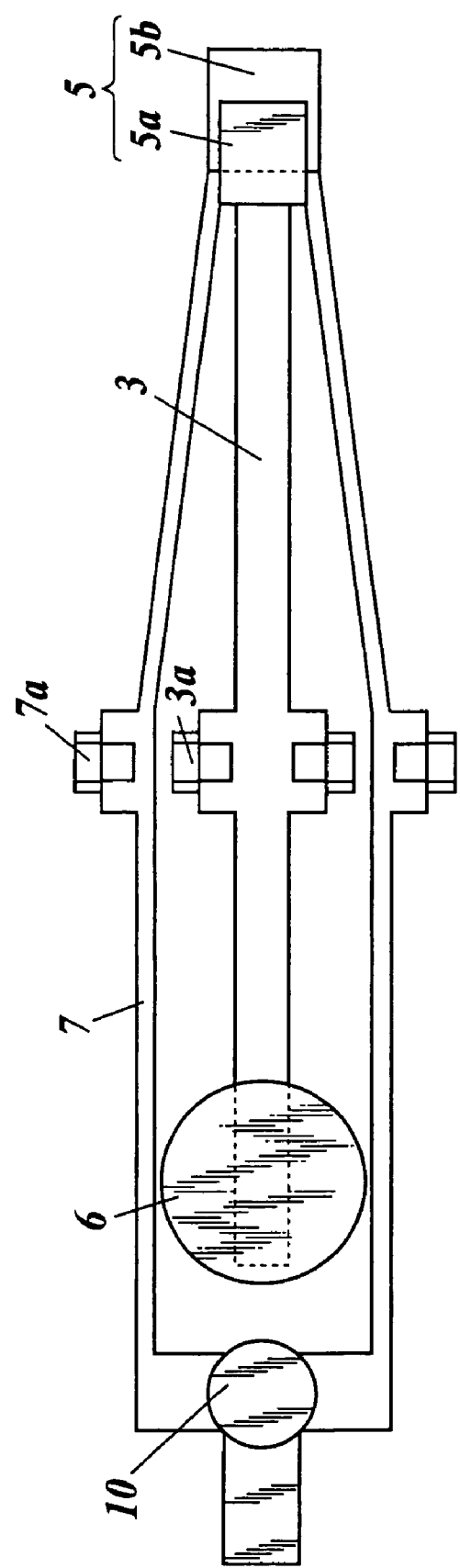
FIG. 2 is a top view showing a lever portion of the indentation testing instrument.
Figure 3:
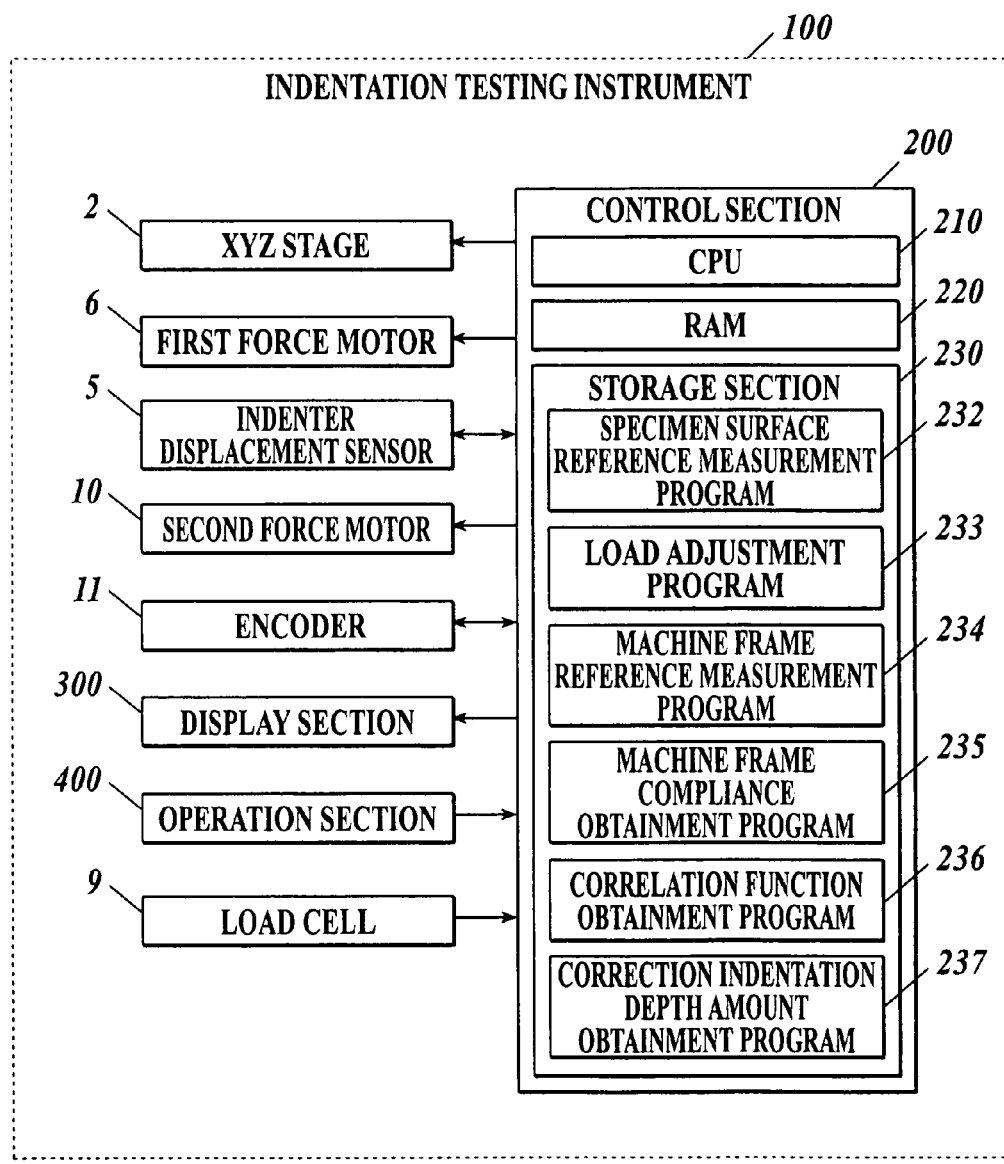
FIG. 3 is a block diagram showing a main construction of the indentation testing instrument according to the present invention.

The indentation testing instrument 100 is composed of a testing device body 1 to apply the test force (load) to a specimen S, a control section 200 to control each section of the testing device body 1, a display section 300, an operation section 400 and the like, as shown in FIGS. 1-3.

The testing device body 1 includes: a specimen holding stage 2 on which the specimen S is placed; a loading lever 3 supported pivotally by the testing device body 1; an indenter 4 provided on a lower surface of one end side of the loading lever 3; a displacement sensor movable section 5a as an indenter linkage section which is provided on an upper surface of the one end side of the loading lever 3; a first force motor 6 as a loading lever driving section which is provided at the other end side of the loading lever 3; a reference lever 7 supported pivotally by the testing device body 1; a contactor 8 as an indenter reference section which is provided on a lower surface of one end side of the reference lever 7 attachably and detachably; a load cell 9 set between the lower surface of the one end side of the reference lever 7 and the contactor 8; a displacement sensor fixing section 5b as an indenter position detection section which is provided on an upper surface of the one end side of the reference lever 7; a second force motor 10 as a reference lever driving section which is provided on the other end side of the reference lever 7; an encoder 11 as a lever position detection section to detect a displacement amount at the time when the reference lever 7 turns; a stopper 12 touching the other end side of the reference lever 7 and the like.

The specimen holding stage 2 holds the specimen S placed on an upper surface thereof and supports the specimen S to prevent it from moving in a test measurement.

The specimen holding stage 2 is moved from right to left or up and down by a XYZ stage 2a so as to adjust a position of the specimen S with respect to the indenter 4.

The loading lever 3 is supported pivotally by a pivot shaft 3a near a center position of the testing device body 1, and provided with the indenter 4 on the lower surface of the one end side of the loading lever 3. Moreover, the loading lever 3 is provided with the first force motor 6 on the upper surface of the other end side of the loading lever 3.

The first force motor 6 is, for example, composed of a force coil and magnet, and uses a force generated depending on an electromagnetic induction of a magnetic field produced by the magnet and current flowing through the force coil as a drive force to turn the loading lever 3 so that the one end side of the loading lever 3 is pushed down and up. By driving of the first force motor 6, it is possible to push down the one end side of the loading lever 3 to apply the load to the indenter 4 so that the indenter 4 is pressed against a surface of the specimen S.

Moreover, the displacement sensor movable section 5a is provided on the upper surface of the one end side of the loading lever 3. The displacement sensor movable section 5a is moved up and down in conjunction with the indenter 4 which is pushed up and down by the loading lever 3.

The reference lever 7 is supported pivotally by a pivot shaft 7a so as to have a shaft center which is approximately same as that of the loading lever 3. The load cell 9 is provided on the lower surface of the one end side of the reference lever 7, and the contactor 8 is provided under the load cell 9 attachably and detachably. The second force motor 10 is provided on the upper surface of the other end side of the reference lever 7.

Incidentally, as shown in FIG. 2, the reference lever 7 is placed so as to surround the loading lever 3 as seen from top surface, and has a roughly frame shape.

The second force motor 10 is, for example, composed of a force coil and magnet, and uses a force generated depending on an electromagnetic induction of a magnetic field produced by the magnet and current flowing through the force coil as a drive force to turn the reference lever 7 so that the one end side of the reference lever 7 is pushed down and up.

The displacement sensor fixing section 5b, which detects a displacement amount at the time when the displacement sensor movable section 5a of the loading lever 3 moves, is provided on the upper surface of the one end side of the reference lever 7.

For example, the displacement sensor movable section 5a is an electrode plate having a roughly U-shaped cross section, and the displacement sensor fixing section 5b is an electrode plate sandwiched separately by U-shaped portion of the displacement sensor movable section 5a. The displacement sensor movable section 5a and the displacement sensor fixing section 5b constitute together an indenter displacement sensor 5.

Specifically, the indenter displacement sensor 5 is a sensor to measure a movement amount (displacement amount) of the indenter 4 by a capacitance method. The indenter displacement sensor 5 measures the displacement amount of the indenter 4 based on a capacitance between the electrode plates which changes depending on a distance between the displacement sensor movable section 5a and the displacement sensor fixing section 5b.

In other words, the indenter displacement sensor 5 measures the displacement amount of the indenter 4 by measuring a displacement of the displacement sensor movable section 5a with respect to the displacement sensor fixing section 5b. Incidentally, the indenter displacement sensor 5 outputs data (signal) regarding the measured displacement amount of the indenter 4 to the control section 200.

The contactor 8 is provided on the lower surface of the one end side of the reference lever 7. The contactor 8 is a member as a positional reference of a tip portion of the indenter 4 provided on the lower surface of the one end side of the loading lever 3.

The load cell 9 is provided on the lower surface of the one end side of the reference lever 7. The load cell 9 is a sensor to measure a pressing force by the one end side of the reference lever 7 touching the specimen S when the indenter 4 is pushed down so as to measure the load by the reference lever 7 pressed against the specimen S. The load cell 9 outputs data (signal) regarding the measured load to the control section 200.

Incidentally, since the contactor 8 sometimes prevents the movement of the loading lever 3 in some measurement methods for pressing the indenter 4 against the specimen S, the contactor 8 is provided on the lower surface of the one end side of the reference lever 7 attachably and detachably so as to be removed in such situations.

The encoder 11 is a sensor to detect a displacement amount at the time when the reference lever 7 turns. The encoder 11 corrects a reduction of a pressing force due to a torsional rigidity of a supporting point 7a result from sinking of the specimen when the test force is applied.

In other words, the encoder 11 detects a rotation angle of the reference lever 7 in the state that the contactor 8 touches the specimen surface so as to correct the reduction of the pressing force due to the torsional rigidity of the supporting point 7a result from sinking of the specimen when the test force is applied. Incidentally, the encoder 11 outputs data (signal) regarding the displacement amount of the reference lever 7 depending on the detected rotational angle of the reference lever 7, to the control section 200.

The stopper 12 is a member touching the upper surface of the other end side of the reference lever 7 so as to define a reference position of the reference lever 7.

The stopper 12 is, for example, composed of a micrometer head and capable of height adjustment by turning a feed screw. In other words, by performing the height adjustment of the stopper 12, it is possible to adjust the rotational angle of the reference lever 7 touching the stopper 12, and to adjust the stopper 12 so as not to touch the reference lever 12.

The display section 300 is a liquid crystal panel, for example, and performs displaying processing of various display screens such as the test result according to a display signal input from the control section 200.

The operation section 400 is an operation key group such as a keyboard, for example, and outputs an operation signal associated with a user operation to the control section 200 when a user operates the operation section 400. Incidentally, the operation section 400 may include other operation devices such as pointing devices including a mouse and a touch panel, and remote controller, as appropriate.

The operation section 400 is operated when a user inputs an instruction to perform the indentation test of the specimen S.

The control section 200 includes a CPU 210, RAM 220, and storage section 230, as shown in FIG. 3. The control section 200 is connected to the XYZ stage 2a, the first force motor 6, the indenter displacement sensor 5, the second force motor 10, the encoder 11, the display section 300, the operation section 400 and the like, through a system bus and the like.

The CPU 210 performs various control processings according to various processing programs for the indentation testing instrument stored in the storage section 230, for example.

The RAM 220 includes a program storage area for expanding a processing program to be executed by the CPU 210, and a data storage area for storing input data, a processing result generated as executing the processing program, and the like, for example.

The storage section 230 stores a system program executable in the indentation testing instrument 100, various processing programs executable by the system program, data to be used when the various processing programs are executed, data of various processing results arithmetic-processed by the CPU 210, and the like, for example. Incidentally, the programs are stored in the stored section 230 in the form of a computer-readable program code.

Specifically, the storage section 230 stores a specimen surface reference measurement program 232, a load adjustment program 233, a machine frame reference measurement program 234, a machine frame compliance obtainment program 235, a correlation function obtainment program 236, a correction indentation depth amount obtainment program 237 and the like, for example.

The specimen surface reference measurement program 232 is a program to allow the CPU 210 to realize a function to turn the loading lever 3 from the state that the tip portion of the indenter 4 and the contactor 8 touch the specimen surface so as to measure a first indentation depth amount at the time when the indenter 4 is pressed against the specimen S by detecting the displacement amount of the displacement sensor movable section 5a with the displacement sensor fixing section 5b.

In other words, the CPU 210 functions as a specimen surface reference measurement member to allow the first force motor 6 to drive to turn the loading lever 3 so as to measure the first indentation depth amount at the time when the indenter 4 provided in the loading lever 3 is pressed against the specimen S by detecting the displacement amount of the indenter 4 measured by the indenter displacement sensor 5, by executing the specimen surface reference measurement program 232.

Figure 4A:
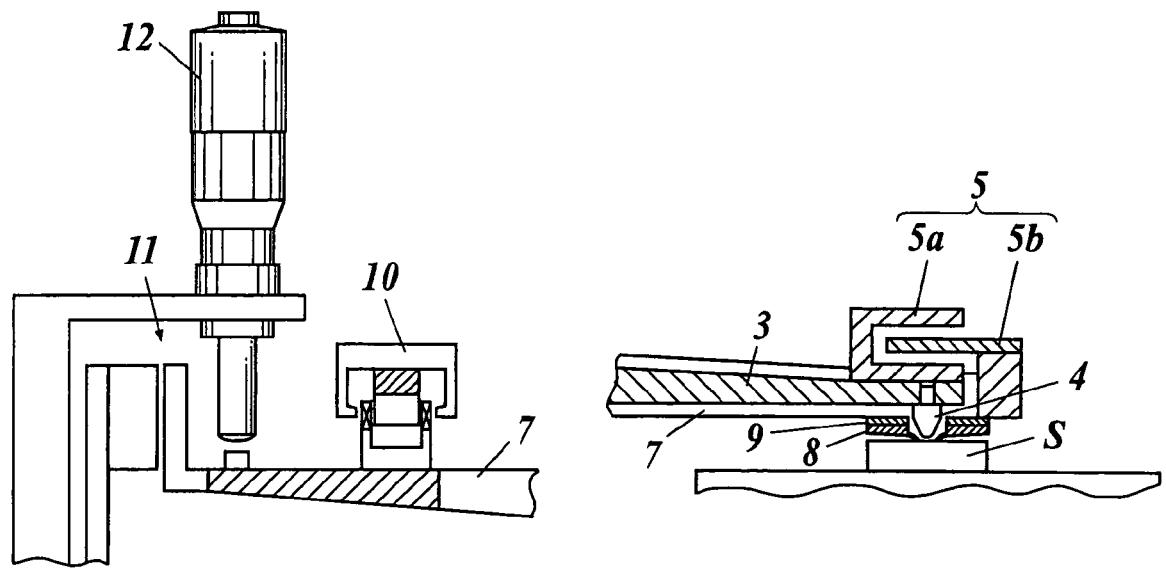
FIG. 4A is an enlarged view of a main part of the indentation testing instrument showing a configuration at the time of a specimen surface reference measurement.

Specifically, as shown in FIG. 4A, the CPU 210 presses the indenter 4 against the specimen S from the state that the stopper 12 is adjusted to a position located apart from the reference lever 7 and the contactor 8 touches the specimen S, to measure the indentation depth amount.

Incidentally, since the method where the CPU 210 as the specimen surface reference measurement member rotates the loading lever 3 from the state that the tip portion of the indenter 4 and the contactor 8 touch the specimen surface and measures the first indentation depth amount when the indenter 4 is pressed against the specimen S is same as a specimen surface reference type measurement method where a displacement reference of the indenter 4 is the surface of the specimen S, the displacement amount of the indenter 4 equivalent to the first indentation depth amount measured by the CPU 210 as the specimen surface reference measurement member does not include a machine frame compliance.

Moreover, when the indenter 4 declines toward the specimen S, since decline displacement amounts before and after the indenter 4 contacts the specimen S are different and a changing point of the decline displacement amount is a contact point of the indenter 4 and the specimen S, the displace amount after the contact point is measured as the indentation depth amount.

The load adjustment program 233 is a program to allow the CPU 210 to realize a function to adjust the load for pressing the contactor 8 against the specimen S to be constant while the CPU 210 as the specimen surface reference measurement member measures the first indentation depth amount.

In other words, the CPU 210 functions as a load adjustment member to adjust an output of the second force motor 10 to adjust driving of the reference lever 7 so as to adjust the load for pressing the contactor 8 against the specimen S to be constant, by executing the load adjustment program 233.

Specifically, the CPU 210 as the load adjustment member adjusts turning of the reference lever 7 so that the load for pressing the contactor 8 against the specimen S, which is a pressing force at the time when the reference lever 7 pushes down the contactor 8 measured by the load cell 9, is constant, thereby the load for pressing the contactor 8 against the specimen S is adjusted to be constant.

The machine frame reference measurement program 234 is a program to allow the CPU 210 to realize a function to turn the loading lever 3 from the state that the contactor 8 as the indenter reference section is removed and the reference lever 7 touches the stopper 12 to measure a second indentation depth amount at the time when the indenter 4 is pressed against the specimen S.

In other words, the CPU 210 functions as a machine frame reference measurement member to drive the first force motor 6 and the second force motor 10 to turn the loading lever 3 to measure the second indentation depth amount at the time when the indenter 4 provided in the loading lever 3 is pressed against the specimen S by detecting the displacement amount of the indenter 4 measured by the indenter displacement sensor 5, by executing the machine frame reference measurement program 234.

Figure 4B:
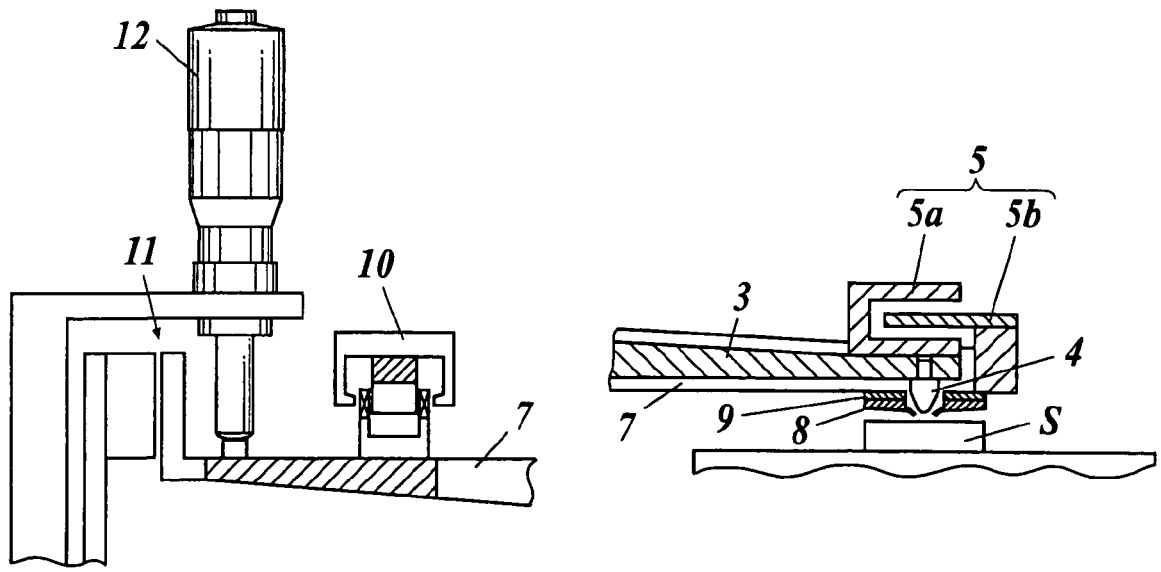
FIG. 4B is an enlarged view of a main part of the indentation testing instrument showing a configuration at the time of a machine frame reference measurement.

Specifically, as shown in FIG. 4B, the CPU 210 presses the indenter 4 against the specimen S from the state that the stopper 12 is adjusted to a position touching the reference lever 7 and the contactor 8 is spaced apart from the surface of the specimen S, to measure the indentation depth amount. Incidentally, in FIG. 4B, in order to show a distance between the contactor 8 and the specimen S, the state that the contactor 8 is attached is illustrated for explaining. Even in the state that the contactor 8 is removed, an arrangement of the stopper 12 and the reference lever 7 is the same as the arrangement thereof shown in FIG. 4B.

Incidentally, the displacement amount at the time when the CPU 210 as the machine frame reference measurement member rotates the loading lever 3 from the state that the contactor 8 is removed and the reference lever 7 touches the stopper 12 is equivalent to the displacement amount of the indenter 4. Thus, the method for measuring the second indentation depth amount by the CPU 210 as the machine frame reference measurement member includes the machine frame compliance.

The machine frame compliance obtainment program 235 is a program to allow the CPU 210 to realize a function to obtain the machine frame compliance of the indentation testing instrument 100 by subtracting the first indentation depth amount measured by the CPU 210 as the specimen surface reference measurement member from the second indentation depth amount measured by the CPU 210 as the machine frame reference measurement member.

In other words, the CPU functions as a machine frame compliance obtainment member to obtain the machine frame compliance of the indentation testing instrument 100 by perform the processing to subtract the displacement amount of the indenter 4 which does not includes the machine frame compliance, corresponding to the first indentation depth amount measured by the CPU 210 as the specimen surface reference measurement member, from the displacement of the indenter 4 which includes the machine frame compliance, corresponding to the second indentation depth amount measured by the CPU 210 as the machine frame reference measurement member, by executing the machine frame compliance obtainment program 235.

Incidentally, data regarding the machine frame compliance measured by the CPU as the machine frame reference measurement member is stored in the RAM 220 or a predetermined memory (for example, a semiconductor memory or EEPROM).

The correlation function obtainment program 236 is a program to allow the CPU to realize a function to obtain the machine frame compliance obtained by the CPU 210 as the machine frame reference measurement member, which is the machine frame compliance of each of the loads when the indenter 4 is pressed against the specimen S with various loads, to obtain a correlation function between the load and the machine frame compliance.

Figure 5:
FIG. 5 is an explanatory view showing an example of a correlation function between a load and a machine frame compliance.

In other words, the CPU functions as a correlation function obtainment member to obtain the correlation function between the load and the machine frame compliance by plotting a graph of the machine frame compliance with respect to the loads at the time when the indenter 4 is pressed against the specimen S with various loads (see FIG. 5), by executing the correlation function obtainment program 236.

Incidentally, data regarding the correlation function obtained by the CPU as the correlation function obtainment member is stored in the RAM 220 or a predetermined memory (for example, a semiconductor memory or EEPROM).

The correction indentation depth amount obtainment program 237 is a program to allow the CPU 210 to realize a function to obtain the corrected indentation depth amount by subtracting the machine frame compliance at the time of measuring the second indentation depth amount from the second indentation depth amount with respect to an arbitrary load measured by the CPU 210 as the machine frame reference measurement member based on the correlation function obtained by the CPU 210 as the correlation function obtainment member.

In other words, the CPU 210 functions as a correction indentation depth amount obtainment member to obtain the corrected indentation depth amount by obtaining the machine frame compliance corresponding to the load at the time when the CPU 210 as the machine frame reference measurement member measures the second indentation depth amount based on the correlation function obtained by the CPU 210 as the correlation function obtainment member and subtracting the machine frame compliance from the second indentation depth amount, by executing the correction indentation depth amount obtainment program 237.

Figure 6:
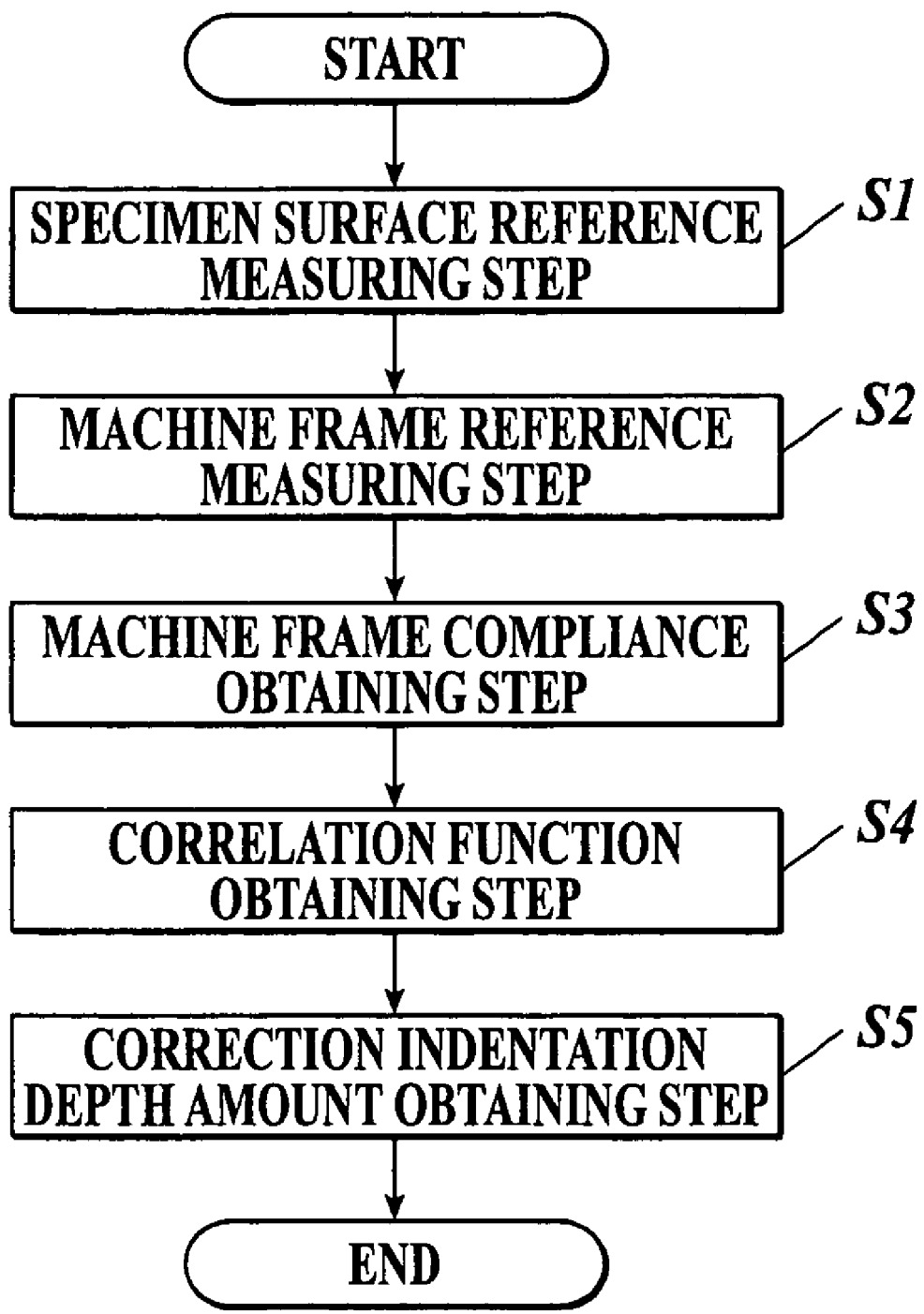
FIG. 6 is a flowchart showing main steps regarding an indentation testing method with the indentation testing instrument according to the present invention.

Next, an indentation testing method by the indentation testing instrument according to the present invention will be described based on a flowchart shown in FIG. 6.

Firstly, the loading lever 3 and the reference lever 7 turn to the position where the tip portion of the indenter 4 and the contactor 8 contact with the surface of the specimen S placed on the specimen holding stage 2 of the indentation testing instrument 100, then only the loading lever 3 turns so that the indenter 4 is pressed against the specimen S, and the indenter displacement sensor 5 detects the displacement amount of the indenter 4 according to the specimen surface reference measuring method, which is the first indentation depth amount as pressing the indenter 4 (Step S1; specimen surface reference measuring step).

In other words, the CPU 210 measures the displacement amount of the indenter 4 by measuring the displacement of the displacement sensor movable section 5a provided in the loading lever 3 which turns with the displacement sensor fixing section 5b of the indenter displacement sensor 5 provided on the reference lever 7 which does not move in the state that the contactor 8 touches the surface of the specimen S.

Incidentally, in Step S1, the displacement amounts of the indenter 4 which are the first indentation depth amounts when the indenter 4 is pressed against the specimen S with the various loads are measured so that the displacement amounts of the indenter 4 according to the specimen surface reference measuring method are stored in a predetermined memory while correlating them to the loads respectively.

Then, in the state that the contactor 8 is removed from the reference lever 7, the loading lever 3 turns from the state the reference lever touches the stopper, toward the specimen S placed on the specimen holding stage 2, and the indenter displacement sensor 5 detects the displacement amount of the indenter 4 according to the machine frame reference measuring method, which is the second indentation depth amount at the time when the indenter 4 is pressed against the specimen S (Step S2; machine frame reference measuring step).

Incidentally, in Step S2, the displacement amounts of the indenter 4 which are the second indentation depth amounts at the time when the indenter 4 is pressed against the specimen S with the various loads are measured so that the displacement amounts of the indenter 4 according to the machine frame reference measuring method are stored in a predetermined memory while correlating them to the loads respectively.

Then, the CPU 210 obtains the machine frame compliance of the indentation testing instrument 100 by subtracting the displacement amount of the indenter 4 equivalent to the first indentation depth amount measured by the CPU 210 according to the specimen surface reference measuring method from the displacement amount of the indenter 4 equivalent to the second indentation depth amount measured by the CPU 210 according to the machine frame reference measuring method (Step S3; machine frame compliance obtaining step).

Incidentally, here the machine frame compliance with respect to each of the various load are calculated and obtained based on the first indentation depth amounts and the second indentation depth amounts corresponding to the various loads measured and obtained in Step S1 and Step S2.

Next, the CPU 210 plots the graph of the obtained machine frame compliance of each of the loads with respect to the load to obtain the correlation function between the load and the machine frame compliance (Step S4; correlation function obtaining step).

By obtaining the correlation function between the load and the machine frame compliance, it becomes possible to obtain the machine frame compliance with respect to an arbitrary load.

Next, the CPU 210 measures the displacement amount of the indenter 4 equivalent to the second indentation depth with respect to an arbitrary load, obtains the machine frame compliance corresponding to the arbitrary load based on the correlation function obtained in Step S4, and calculates and obtains the corrected indentation depth amount by subtracting the machine frame compliance from the displacement amount of the indenter measured by the machine frame reference measuring method (Step S5; correction indentation depth amount obtaining step).

Incidentally, the corrected indentation depth amount obtained by the CPU 210 is displayed as a test result on the display section 300.

As described above, since the indentation testing instrument 100 according to the present invention includes the loading lever 3 and the reference lever 7 and can measure the displacement amount (the first indentation depth amount) of the indenter 4 according to the specimen surface reference measuring method and the displacement amount (the second indentation depth amount) of the indenter 4 according to the machine frame reference measuring method, it is possible to obtain the machine frame compliance of the indention testing instrument 100 by calculating a difference ("the second indentation depth amount"—"the first indentation depth amount") between the displacement amounts.

Moreover, by obtaining the machine frame compliance with respect to each of the loads at the time when the indenter 4 is pressed against the specimen S with various loads to obtain the correlation function between the load and the machine frame compliance, it becomes possible to obtain the machine frame compliance with respect to an arbitrary load based on the correlation function. Then, by subtracting the machine frame compliance corresponding to the load at the time of measuring the second indentation depth amount from the displacement amount of the indenter 4 equivalent to the second indentation depth amount measured with the arbitrary load, it is possible to calculate and obtain the corrected indentation depth amount.

Thus, by the indentation testing method with the indentation testing instrument 100, the proper machine frame compliance can be obtained by subtracting the displacement amount (the first indentation depth amount) of the indenter 4 according to the specimen surface reference measuring method from the displacement amount (the second indentation depth amount) of the indenter 4 according to the machine frame reference measuring method, and it is possible to obtain the proper machine frame compliance with respect to an arbitrary load based on the obtained correlation function.

Therefore, by the indentation testing method with the indentation testing instrument 100, it becomes possible to obtain the proper machine frame compliance, and to obtain the corrected indentation depth amount based on the proper machine frame compliance. Moreover, since it becomes possible to measure the indentation depth amount while eliminating an influence of the machine frame compliance so as to obtain the corrected indentation depth amount, an evaluation of a mechanical property such as a hardness of material can be performed more precisely.

Incidentally, the present invention is not limited to the above embodiment.

Figure 7A:
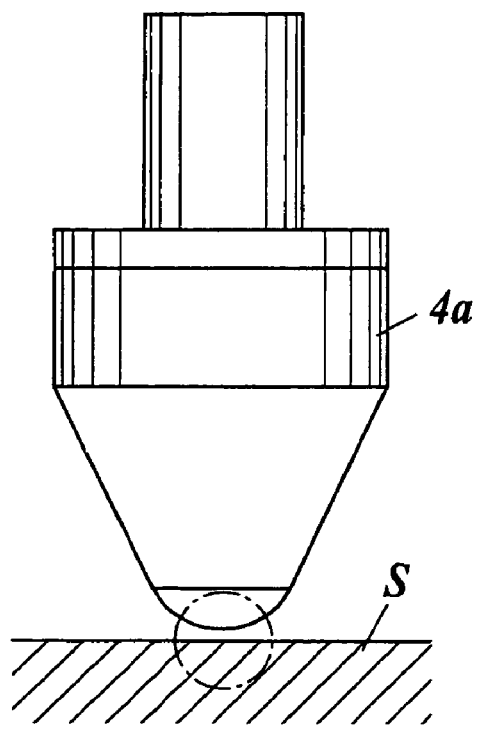
FIG. 7A is a side view showing a correction indenter.
Figure 7B:
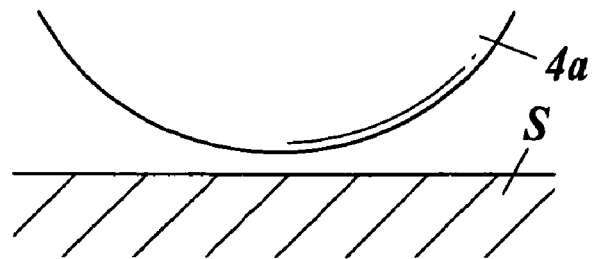
FIG. 7B is an enlarged view of a tip portion of the correction indenter.

For example, as shown in FIG. 7, a correction indenter 4a which allows the specimen S to deform elastically, not plastically, can be set as the indenter of the indentation testing instrument 100.

As the correction indenter 4a, for example, as shown in FIG. 7, an indenter a tip of which has a spherical shape of large curvature can be used.

Figure 8:
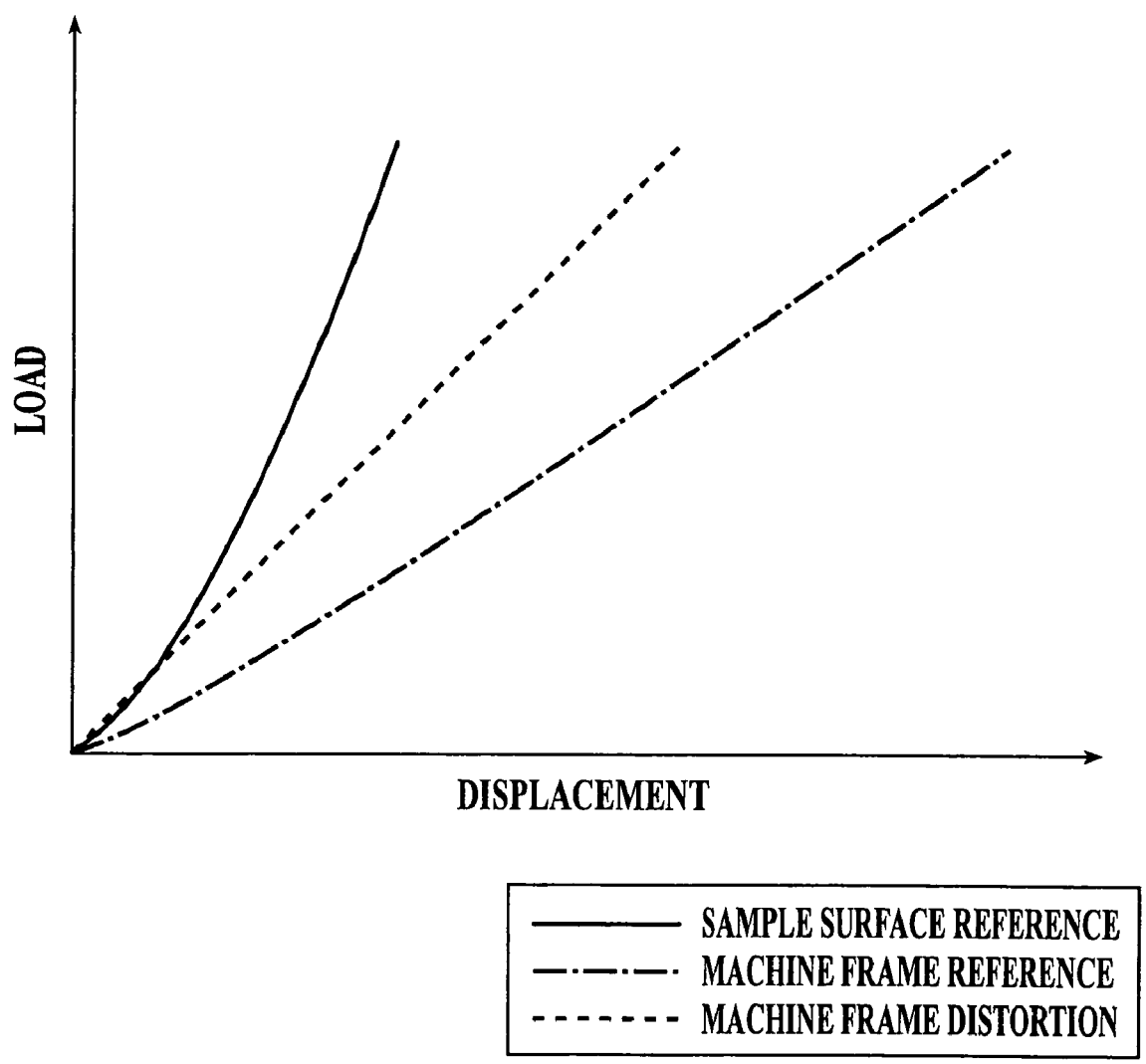
FIG. 8 is an explanatory view regarding the machine frame compliance at the time when an indentation test is performed in an elastic deformation area in the specimen to remove an influence of a measurement error occurring between loading and unloading.

Thus, when the indentation test is performed in an elastic deformation region of the specimen S with the correction indenter 4a for allowing the specimen S to elastically deform, as shown in FIG. 8, it is possible to remove an influence of a measurement error occurring between loading and unloading because of the plastic deformation of the specimen S. As a result, a more precise machine frame compliance can be obtained by calculating a difference between the displacement amount in the machine frame reference and the displacement amount in the specimen surface reference, and more precise measurement of the specimen S can be performed.

Moreover, although in the above embodiment the machine frame reference measurement program 234 is a program to allow the CPU 210 to realize a function to turn the loading lever 3 from the state that the contactor 8 as the indenter reference section is removed and the reference lever 7 touches the stopper 12 to measure the second indentation depth amount at the time when the indenter 4 is pressed against the specimen S and the CPU 210 as the machine frame reference measuring member measures the second indentation depth amount at the time when the indenter 4 is pressed against the specimen S in the state of the contactor 8 is removed, the present invention is not limited to above. For example, the test can be performed in a method of measuring the second indentation depth amount at the time when the loading lever 3 turns from the state that the reference lever 7 touches the stopper 12 while the contactor 8 is attached to the reference lever 7.

Incidentally, a measurement of the second indentation depth amount by a method where the contactor 8 is not remover is performed by turning the loading lever 3 from the state that the reference lever 7 touches the stopper 12 in a state (position) where the contactor 8 does not touch the specimen surface to press the indenter 4 against the specimen S.

Moreover, although in the above embodiment the method using the load cell 9 and the method using the encoder as adjustment members of the load for pressing the reference lever, the present invention is not limited to this.

Furthermore, for example, by using a knife-edge as the supporting point to match a gravity center in X-Y direction of the reference lever 7 and a rotation center, a posture of the reference lever 7 may change and the pressing force may be constant. By this method, since a spring is not used as the supporting point, the pressing force does not change due to the torsional rigidity.

It is needless to say that specific detail configuration and the like can also be changed arbitrarily.

According to a first aspect of the preferred embodiment of the present invention, an indentation testing instrument includes: a loading lever supported pivotally; an indenter provided on a lower surface of one end side of the loading lever; an indenter linkage section provided on an upper surface of the one end side of the loading lever, which indenter linkage section is associated with the indenter; a loading lever driving section provided on the other end side of the loading lever, which loading lever driving section turns the loading lever; a reference lever supported pivotally so as to have a shaft center which is approximately same as a shaft center of the loading lever; an indenter reference section provided on a lower surface of one end side of the reference lever, which indenter reference section is a positional reference of a tip portion of the indenter; an indenter position detection section provided on an upper surface of the one end side of the reference lever, which indenter position detection section detects a displacement amount of the indenter linkage section; a reference lever driving section provided on the other end side of the reference lever, which reference lever driving section turns the reference lever; a stopper to stop the reference lever so that the indenter reference section is in a predetermined position with respect to the specimen surface; a specimen surface reference measurement member to turn the loading lever from the state that the indenter reference section touches the specimen surface, and to measure a first indentation depth amount at the time when the indenter touching the specimen surface is pressed against the specimen by detecting the displacement amount of the indenter linkage section with the indenter position detection section; and a machine frame reference measurement member to turn the loading lever from the state that the reference lever touches the stopper and the indenter reference section is spaced apart from the specimen surface, and to measure a second indentation depth amount at the time when the indenter touching the specimen surface is pressed against the specimen.

Preferably, the indenter reference section is provided on the lower surface on the one end side of the reference lever attachably and detachably.

Preferably, the indentation testing instrument further includes: a load adjustment member to adjust the load for pressing the indenter reference section against the specimen to be constant while the specimen surface reference measurement member measures the first indentation depth amount.

According to a second aspect of the preferred embodiment of the present invention, an indentation testing method in the indentation testing instrument includes: obtaining a machine frame compliance of the indentation testing instrument by subtracting the first indentation depth amount measure by the specimen surface reference measurement member from the second indentation depth amount measured by the machine frame reference measurement member; obtaining a correlation function between the load and the machine frame compliance by obtaining the machine frame compliance with respect to each of the load for pressing the indenter against the specimen in the machine frame compliance obtaining step; obtaining a corrected indentation depth amount by subtracting the machine frame compliance with respect to the loading as measuring the second indentation depth amount from the second indentation depth amount with respect to an arbitrary load measured by the machine frame reference measurement member based on the correlation function obtained in the correlation function obtaining step.

Preferably, the machine frame compliance of the indentation testing instrument is obtained by providing a correction indenter for elastically deforming the specimen in the indentation testing instrument when the machine frame compliance is obtained in the machine frame compliance obtaining step, pressing the correction indenter against the specimen, and subtracting the displacement amount of the indenter linkage section detected with the indenter position detection section in the specimen surface reference measurement member from the displacement amount of the reference lever detected with a lever position detection section in the machine frame reference measurement member.

According to the present invention, the indentation testing instrument includes the loading lever which is provided with the indenter, and the reference lever which is provided with the indenter reference section as the positional reference of the indenter and is associated with the loading lever. The indentation testing instrument can measure the first indentation depth amount equivalent to the displacement amount of the indenter according to the specimen surface reference measuring method by turning the loading lever from the state that the indenter reference section touches the specimen surface to press the indenter against the specimen, and can measure the second indentation depth amount equivalent to the displacement amount of the indenter according to the machine frame reference measuring method by turning the loading lever from the state that the reference lever touches the stopper to press the indenter against the specimen. Then, the indentation testing instrument can obtain the machine frame compliance by subtracting the displacement amount (the first indentation depth amount) of the indenter according to the specimen surface reference measuring method from the displacement amount (the second indentation depth amount) of the indenter according to the machine frame reference measuring method.

Moreover, for example, since the correlation function between the load and the machine frame compliance can be obtained by obtaining the machine frame compliance with respect to each of the loads at the time of when the indenter is pressed against the specimen with the various loads, the machine frame compliance with respect to a arbitrary load can be obtain based on the correlation function.

Therefore, the corrected indentation depth amount can be calculated and obtained by obtaining the machine frame compliance corresponding to the arbitrary load as measuring the second indentation depth amount based on the correlation function when the second indentation depth amount is measured with an arbitrary load, and by subtracting the obtained machine frame compliance from the displacement amount of the indenter equivalent to the second indentation depth amount measured with the arbitrary load.

Thus, by the indentation testing method with the indentation testing instrument, the proper machine frame compliance can be obtained by subtracting the displacement amount (the first indentation depth amount) of the indenter according to the specimen surface reference measuring method from the displacement amount (the second indentation depth amount) of the indenter according to the machine frame reference measuring method, and it is possible to obtain the proper machine frame compliance with respect to an arbitrary load based on the obtained correlation function.

Moreover, since it becomes possible to measure the indentation depth amount while eliminating an influence of the machine frame compliance so as to obtain the corrected indentation depth amount, an evaluation of a mechanical property such as a hardness of material can be performed more precisely.

The entire disclosure of Japanese Patent Application No. 2007-334489 filed on Dec. 26, 2007, including specification, claims, drawings and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. An indentation testing instrument comprising:
    a loading lever supported pivotally;
    an indenter provided on a lower surface of a first end of the loading lever;
    a displacement sensor movable section provided on an upper surface of the first end of the loading lever, the displacement sensor movable section being associated with the indenter;
    a loading lever driving section provided on an opposite end of the loading lever, the loading lever driving section configured to turn the loading lever;
    a reference lever supported pivotally so as to have a shaft center that is approximately the same as a shaft center of the loading lever;
    a contactor provided on a lower surface of a first end of the reference lever, the contactor being a positional reference of a tip portion of the indenter;
    a displacement sensor fixing section provided on an upper surface of the first end of the reference lever, the displacement sensor fixing section configured to detect a displacement amount of the displacement sensor movable section;
    a reference lever driving section provided on an opposite end of the reference lever, the reference lever driving section configured to turn the reference lever;
    a stopper to stop the reference lever so that the contactor is in a predetermined position with respect to a specimen surface;
    a specimen surface reference measurement member configured to turn the loading lever from a state that the contactor touches the specimen surface, and configured to measure a first indentation depth amount at a time when the indenter touching the specimen surface is pressed against the specimen by detecting the displacement amount of the displacement sensor movable section with the displacement sensor fixing section; and
    a machine frame reference measurement member configured to turn the loading lever from a state that the reference lever touches the stopper and the contactor is spaced apart from the specimen surface, and configured to measure a second indentation depth amount at a time when the indenter touching the specimen surface is pressed against the specimen.

2. The indentation testing instrument according to claim 1, wherein the contactor is provided on the lower surface on the first end of the reference lever attachably and detachably.

3. The indentation testing instrument according to claim 1 further comprising:
    a load adjustment member configured to adjust a load for pressing the contactor against the specimen to be constant while the specimen surface reference measurement member measures the first indentation depth amount.

4. An indentation testing method in the indentation testing instrument according to claim 1 comprising:
    obtaining a machine frame compliance of the indentation testing instrument by subtracting the first indentation depth amount measured by the specimen surface reference measurement member from the second indentation depth amount measured by the machine frame reference measurement member;
    obtaining a correlation function between a load and the machine frame compliance by obtaining the machine frame compliance with respect to each load for pressing the indenter against the specimen in the machine frame compliance obtaining step; and
    obtaining a corrected depth amount by subtracting the machine frame compliance from the second indentation depth amount with respect to an arbitrary load, the machine frame compliance corresponding to the arbitrary load based on the correlation function obtained in the correlation function obtaining step.

5. The indentation testing method according to claim 4, wherein the machine frame compliance of the indentation testing instrument is obtained by providing a correction indenter for elastically deforming the specimen in the indentation testing instrument when the machine frame compliance is obtained in the machine frame compliance obtaining step, pressing the correction indenter against the specimen, and subtracting the displacement amount of the displacement sensor movable section detected with the displacement sensor fixing section in the specimen surface reference measurement member from the displacement amount of the reference lever detected with a lever position detection section in the machine frame reference measurement member.

* * * * *